(12) United States Patent
Popp (10) Patent No.: US 11,020,127 B2
(45) Date of Patent: Jun. 1, 2021

(54) POINT-PRESSURE APPLICATION SYSTEM

(71) Applicant: 6:8 Medical Solutions LLC, Havre de Grace, MD (US)

(72) Inventor: Uriah Shane Popp, Havre de Grace, MD (US)

(73) Assignee: 6:8 Medical Solutions LLC, Havre de Grace, MD (US)

( * ) Notice: Subject to any disclaimer, the term of this patent is extended or adjusted under 35 U.S.C. 154(b) by 169 days.

(21) Appl. No.: 16/364,105

(22) Filed: Mar. 25, 2019

(65) Prior Publication Data

US 2019/0290288 A1    Sep. 26, 2019

Related U.S. Application Data

(60) Provisional application No. 62/648,311, filed on Mar. 26, 2018.

(51) Int. Cl.
*A61B 17/132* (2006.01)
*A61B 17/12* (2006.01)

(52) U.S. Cl.
CPC .......... *A61B 17/1325* (2013.01); *A61B 17/12* (2013.01); *A61B 17/132* (2013.01); *A61B 2017/12004* (2013.01)

(58) Field of Classification Search
CPC ... A61B 17/12; A61B 17/132; A61B 17/1325; A61B 2017/12004
See application file for complete search history.

(56) References Cited

U.S. PATENT DOCUMENTS

| 5,139,512 | A | * | 8/1992 | Dreiling | ............. | A61B 17/1325 606/201 |
|---|---|---|---|---|---|---|
| 5,728,120 | A | | 3/1998 | Shani et al. | | |
| 9,492,177 | B2 | | 11/2016 | Saunders et al. | | |
| 2005/0165445 | A1 | | 7/2005 | Buckman et al. | | |
| 2010/0152770 | A1 | * | 6/2010 | Spencer | ............. | A61B 17/1325 606/203 |
| 2012/0150215 | A1 | * | 6/2012 | Donald | ............. | A61B 17/1327 606/203 |
| 2016/0206298 | A1 | | 7/2016 | Keene et al. | | |

FOREIGN PATENT DOCUMENTS

| CN | 201814618 U | 5/2011 |
|---|---|---|
| CN | 204106109 U | 1/2015 |

* cited by examiner

*Primary Examiner* — Melanie R Tyson
(74) *Attorney, Agent, or Firm* — Shah IP Law, PLLC (57) ABSTRACT

An apparatus for applying point-pressure to a wound site that helps occlude open blood vessels includes a pressure applicator, a mounting plate, articulating strap attachment points, and counter-pressure cavities. The articulating strap attachment points attach to straps around a patient's body so that the apparatus is stabilized over a patient's wound. Moreover, the counter-pressure cavities permit a user to apply leverage caused by counter-force mechanism (while also applying a downward force on the pressure applicator). These features enable a user to quickly and easily apply point pressure to a wound site.

18 Claims, 7 Drawing Sheets

POINT-PRESSURE APPLICATION SYSTEM

CROSS-REFERENCE TO RELATED APPLICATIONS

This application claims priority to U.S. Provisional Patent Application Ser. No. 62/648,311, filed Mar. 26, 2018, entitled "Point pressure and hemorrhage control device." The entire content of that application is incorporated herein by reference.

BACKGROUND

Field of the Art

The present invention pertains to a system for applying point pressure. More specifically, the present disclosure pertains to a point pressure applicator that may be used for limiting hemorrhage by occluding open wounds, blood vessels, etc., or for other medical and/therapeutic uses.

Discussion of the State of the Art

Hemorrhages that are caused by open blood vessels or wounds, which represent a significant danger to patients because they can result in exsanguination. Short term arterial blood loss can be irreversible and may lead to death if left unaddressed. The traditional method for treating hemorrhages is to apply a tourniquet, which wraps around a patient's injured limb and applies constrictive force around the patient's entire limb in an effort to occlude damaged blood vessels and prevent them from bleeding further.

However, traditional tourniquet systems can not be applied to truncal (or non-limbic) portions of a patient's body. For example, traditional tourniquets are ineffective at stopping bleeding—in the pelvic region, the chest, the shoulder, the stomach, etc. Moreover, traditional tourniquets, when applied properly often damage surrounding tissues because of the excessive pressure that may be required in order to achieve vessel occlusion. This ancillary damage may be exacerbated if nearby organs have already suffered trauma. As such, traditional tourniquets sometimes are avoided and some physicians regard them as doing more harm than good.

Some prior art systems have attempted to alleviate this problem by applying point pressure directly to the injured vessels. These systems apply downward pressure directly on the injured vessel instead of applying constrictive force around the entire limb. These systems are much more effective at stopping hemorrhages to junctional locations, and tend to cause less damage to nearby areas. However, these point pressure systems also suffer from significant other limitations. For one, these systems cannot be deployed very quickly. Generally, users or medical care providers must receive extensive training to use these devices, and they are not intuitive in design. They must be properly positioned with a series of screws, air bladders, and straps making repositioning very timely. Thereafter, medical care providers must apply pressure by screwing in a point-pressure applicator, or pump an air bladder, or using a pneumatic pressure application system, which can be affected during aeromedical evacuation from atmospheric pressure. The entire process can take valuable time, or have limitations, which may be critical in saving the patient's life.

However, presently available point-pressure systems are unusable in a variety of different field or transport situations. For example, presently available point-pressure systems rely on a long, vertical rods with a counter foot plate that apply downward pressure to one or more blood vessels. However, these vertical rods with foot plate, because they rely on a stable laying surface, may fall out of place if, for example, a patient moves, if the patient is moved from one location to another, if the rods is accidentally knocked over by a nearby person, or if the patient is being transported in a vehicle that is moving, such as a transport truck or an aerial vehicle. Pneumatic pressure systems and air bladders are similarly limited. For example, air bladders are affected by changes in atmospheric pressure (such as during aeromedical evacuation environments) and the materials used in these devices do not fare well in extreme temperature storage variances, such as the ones that military equipment must endure.

These problems are exacerbated by the fact that it is nearly impossible to use traditional point-pressure systems in a manner that permits the pressure rod to extend vertically above the wound. Human subjects, because of their natural biology, have asymmetric shapes and rounded contours. As a result, in practice, the pressure rod in point-pressure systems rarely extend vertically above a wound. Instead, the pressure rods typically extend above the wound at an angle. This makes the entire system more unstable and more prone to getting knocked over in busy environments.

Finally, traditional tourniquet systems and the newer point-pressure systems are not designed for self-application. These systems require medical professionals to use two hands simultaneously to apply the devices over wounds and to apply pressure once the device is in place. However, single-handed use—and the ability to apply pressure to the patient's own injury—is a critical requirement for military use devices because medical help may not be readily available.

SUMMARY

The present invention is a point-pressure application system that overcomes the limitations described above. More specifically, the present invention is for an auto-locking apparatus for controlling hemorrhage that enables a user to apply point pressure extremely rapidly with a single hand. In one embodiment, the inventive apparatus may be comprised of a mounting plate for mounting the apparatus over a wound site, an articulating strap attachment point that extends from the mounting plate, wherein the articulating strap attachment point may connect to a strap that secures the apparatus over the wound site, a coupling mechanism for coupling the mounting plate to a buckle on the strap that secures the apparatus over the wound site, wherein the coupling mechanism may permit the mounting plate and the buckle to freely rotate around each other when the mounting plate and the buckle are connected to the articulating strap attachment point, wherein the coupling mechanism ensures that the mounting plate remains parallel to the wound site when the apparatus is secured to a patient, a pressure applicator for applying point pressure to the wound site, wherein the pressure applicator extends through the mounting plate and being stabilized in a lateral direction by the mounting plate, an auto-locking mechanism enabling the pressure applicator to travel, upon application of downward force, towards the wound site when the apparatus is placed over the wound site, wherein the auto-locking mechanism prevents the pressure applicator from travelling away from the wound site when downward pressure is removed from the pressure applicator, and wherein the auto-locking mechanism comprising a locking tab, and a finger hold disposed on the mounting plate, wherein the finger hold enables a user to apply counter-force in a generally opposite direction to the downward force that may be applied to the pressure applicator, and wherein the counter-force enables a user to apply leverage when applying downward force to the pressure applicator.

A feature of the present invention is that it enables a user to apply point pressure rapidly. As described above, traditional point-pressure systems employ a screw-in system for slowly moving a pressure rod in a downward direction. This is a reliable method of pressure application. But, it takes times to apply pressure by turning a screw, especially in emergency situations where time is of the essence. The pressure application system of the present invention permits a user to freely slide a pressure applicator in a downward direction by simply applying pressure in a downward direction. The apparatus of the present invention is also comprised of an auto-locking mechanism, which enables the apparatus to maintain pressure even after the user stops applying downward pressure to the pressure applicator.

Another feature of the present invention is that it permits a user to apply pressure by using a single hand, and, as a result, a patient can self-apply the apparatus to his or her own wound in an effort to close it. In one embodiment, the inventive apparatus is comprised of a mounting plate that is further comprised of a finger hold. The finger hold permits a user to apply counter force to the pressure applicator. Without this feature, the user would end up applying pressure to the wound itself. Moreover, without this feature, single-handed application would not be possible.

Another feature of the present invention is that it can be used over any wound site on a patient's body. In one embodiment, the inventive apparatus is comprised of a freely rotating coupling mechanism for coupling the apparatus to straps. More specifically, the coupling mechanism permits the apparatus and/or the straps to rotate freely around each other. This enables a user to secure the straps around any portion of the patient's body, while ensuring that the mounting plate remains over the wound site and remains generally parallel to the wound site. As such, the pressure application maintains its position and applies appropriate downward pressure to occlude a blood vessel or a wound.

Another feature of the present invention is that it stabilizes the apparatus over a wound, which enables users to deploy the inventive apparatus in a field environment. The freely rotating coupling mechanism described above also ensures that the mounting plate remains parallel to the wound.

BRIEF DESCRIPTION OF THE DRAWING FIGURES

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

DETAILED DESCRIPTION

The inventor has conceived, and reduced to practice, an apparatus for applying point pressure. The apparatus may be used for a variety of uses cases, including, for example, to occlude open blood vessels or open wounds, for therapeutic use, such as to apply pressure to acupressure points along a patient's body. Specifically, the inventive apparatus of the present invention is for an auto-locking apparatus, the apparatus enabling a user to apply point pressure extremely rapidly with a single hand. In one embodiment of the invention, the apparatus is comprised of a mounting plate for mounting the apparatus over a wound site, the mounting plate comprising a top surface and a bottom surface, an articulating strap attachment point extending from the mounting plate, the articulating strap attachment point connecting to a strap that secures the apparatus over the wound site, a coupling mechanism for coupling the mounting plate to a buckle on the strap that secures the apparatus over the wound site, the coupling mechanism permitting the mounting plate and the buckle to freely rotate around each other when the mounting plate and the buckle are connected to the articulating strap attachment point, the coupling mechanism ensuring that the mounting plate remains parallel to the wound site when the apparatus is secured to a patient, a pressure applicator for applying point pressure to the wound site, the pressure applicator extending through the mounting plate and being stabilized in a lateral direction by the mounting plate, an auto-locking mechanism enabling the pressure applicator to travel, upon application of downward force, towards the wound site when the apparatus is placed over the wound site, the auto-locking mechanism preventing the pressure applicator from travelling away from the wound site when downward pressure is removed from the pressure applicator, the auto-locking mechanism comprising a locking tab, and a finger hold disposed on the mounting plate, the finger hold enabling a user to apply counter-force in a generally opposite direction to the downward force that may be applied to the pressure applicator, the counter-force enabling a user to apply leverage when applying downward force to the pressure applicator.

In one embodiment, the coupling mechanism of the present invention may be further comprised of locking tab for locking the mounting plate to the strap buckle. The mounting plate may be further comprised of a aperture or opening that extends from the top surface of the mounting plate to the bottom surface of the mounting plate. In one embodiment, the pressure applicator may travel through the aperture or opening in the mounting plate. The pressure applicator may be further comprised of a gripper that is disposed on the distal end of the pressure applicator, the gripper comprised of softer, compressible material. The pressure applicator may also be comprised of a hemorrhage stopper that is disposed on the proximal end of the pressure applicator, the hemorrhage stopper stopping hemorrhage at the wound site upon application of force. The auto-locking mechanism may be further comprised of a tab that is comprised of a aperture or opening, wherein the pressure applicator travels through the aperture or opening in the tab.

In one embodiment of the invention, the locking tab extends at an angle at a resting position, the angle enabling the tab to apply friction to pressure applicator and prevent it from moving longitudinally through tab's aperture or opening. The friction applied on the pressure applicator by the tab may be removed by applying downward pressure on the tab, which places the tab on an plane that is orthogonal to the pressure applicator. In one embodiment, applying downward pressure on the pressure applicator also causes the tab to slide down and become orgthogonal to the pressure applicator, which permits the pressure applicator to freely travel in a downward direction.

In one embodiment of the invention, the tab extends from a tab holder, wherein the tab holder is connected to one end of the tab. Moreover, the tab holder extends from the mounting plate, wherein the tab holder designed to hold the tab, by default, at an offset angle, which enables the tab to apply friction on the pressure applicator. The tab holder may be designed so that it can be depressed at an end that is not connected to the tab holder, thereby placing the tab in a plan that is substantially orthogonal to the pressure applicator.

In one embodiment, the finger hold is molded into the mounting plate. The finger hold may be comprised of a aperture or opening, wherein the pressure applicator travels through the aperture or opening in the mounting plate and the aperture or opening in the finger hold.

In one embodiment, the apparatus may be comprised of four articulating strap attachment points. Each articulating strap attachment point may connect to a buckle, each buckle being connected to a strap. The straps may connect together around a patient to secure the apparatus over a wound site. In one embodiment, the straps may be secured around the patient, the coupling mechanism permits rotation to ensure that the apparatus remains substantially parallel to the surface of the wound site.

The invention is described by reference to various elements herein. It should be noted, however, that although the various elements of the inventive apparatus are described separately below, the elements need not necessarily be separate. The various embodiment may be interconnected and may be cut out of a singular block or mold. The variety of different ways of forming an inventive apparatus, in accordance with the disclosure herein, may be varied without departing from the scope of the invention.

Generally, one or more different embodiments may be described in the present application. Further, for one or more of the embodiments described herein, numerous alternative arrangements may be described, it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices and parts that are connected to each other need not be in continuous connection with each other, unless expressly specified otherwise. In addition, devices and parts that are connected with each other may be connected directly or indirectly through one or more connection means or intermediaries.

A description of an aspect with several components in connection with each other does not imply that all such components are required. To the contrary, a variety of optional components may be described to illustrate a wide variety of possible embodiments and in order to more fully illustrate one or more embodiments. Similarly, although process steps, method steps, or the like may be described in a sequential order, such processes and methods may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, or method is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Alternate implementations are included within the scope of various embodiments in which, for example, functions may be executed out of order from that shown or discussed, including substantially concurrently or in reverse order, depending on the functionality involved, as would be understood by those having ordinary skill in the art.

Overview

Figure 1:
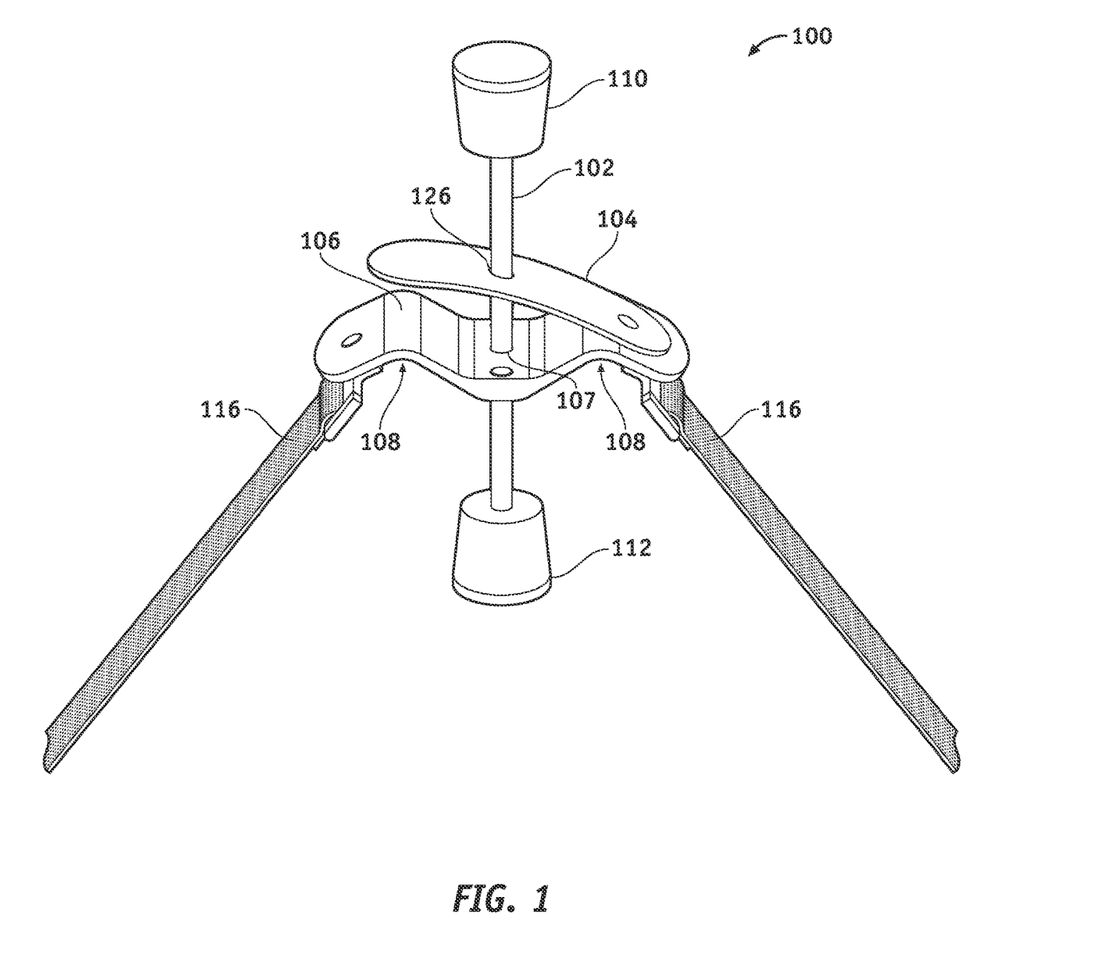
FIG. 1 illustrates, in accordance to one embodiment of the invention, an exemplary inventive apparatus.
Figure 4:
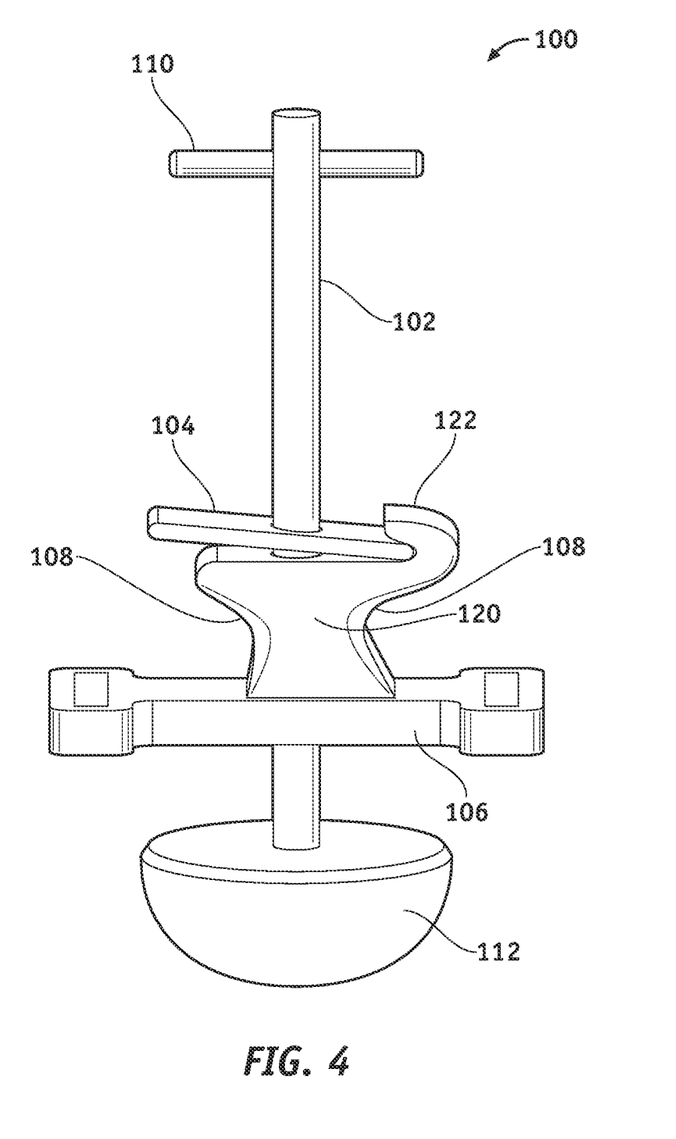
FIG. 4 illustrates an exemplary apparatus, in accordance with another embodiment of the invention.

FIGS. 1 and 4 illustrate two exemplary embodiments of the inventive apparatus 100 disclosed herein. The inventive apparatus 100 is comprised of a mounting plate 106, articulating strap attachment point(s) 114, a pressure applicator 102, a locking tab 104, finger hold(s) 108, and a hemorrhage stopper 112. The apparatus 100 may) be connected to straps 116 via the mounting plate 106 and the articulating strap attachment point(s) 114. FIG. 4 illustrates, in accordance with another exemplary embodiment of the invention, a tab extension portion 120, a tab holder 122, and grip support wings 110.

The various elements assemble together to form the inventive apparatus 100. The entire apparatus 100 may be placed over a wound. Once the apparatus 100 is properly placed, the pressure applicator 102 may be extended, by application of force, in a downward direction towards an open wound or blood vessel. In one embodiment of the invention, the pressure applicator 102 may extend downward until the hemorrhage stopper 112 contacts the open blood vessels and occludes it to prevent it from bleeding further. The finger hold(s) 108 disclosed herein assists a user in applying downward pressure by permitting the user to apply counter-force in an opposite direction (i.e. in an upward direction) to apply leverage to the pressure applicator 102.

The locking tab 104 engages the pressure applicator 102 when external downward pressure is removed from the pressure applicator 102 to prevent the pressure applicator 102 from extending upward or away from the open vessel. The locking tab 104 of the present invention permits the pressure applicator 102 to travel in a downward direction (i.e. toward a wound) upon application of downward force. But it prevents the pressure applicator 102 to travel in an upward direction unless a portion of the locking tab 104 is activated by application of downward force.

In this manner, the apparatus 100 ensures that pressure is maintained on the wound or the injured blood vessel, which prevents the patient from bleeding further. The articulating strap attachment point(s) 114 may be used to connect the apparatus to straps 116 that may be secured against the patient's body. In this manner, the apparatus 100 of the present invention may be used to prevent a patient from bleeding out due to an open wound or injured blood vessels.

Description of Components

The mounting plate 106 of the present invention is designed to be placed above a wound site and/or one or more open blood vessels. The mounting plate 106 serves as the foundation for connecting the various components of the inventive apparatus 100 described herein. Moreover, the mounting plate 106 also serves to stabilize the apparatus 100 over a wound side and serves to redistribute the forces that may be applied by one or more straps 116 when the straps 116 are attached to a patient and the mounting plate 106.

FIGS. 1 and 4 illustrate two exemplary mechanisms for connecting the mounting plate 106 to the locking tab 104. In one exemplary embodiment, as illustrated in FIG. 1, the mounting plate 106 is integrally attached to locking tab 104 via retention device. A variety of different retention devices may be used without departing from the scope of the invention, including, but not limited to a screw, a post, a bracket, etc. As illustrated in FIG. 1, the retention device may connect the mounting plate 106 and the locking tab 104 in a manner that the locking tab 104 may be moved in a downward direction by depressing the locking tab 104 at an end that is not connected to the mounting plate 106, thereby permitting the locking tab 104 to be placed in a plane that is substantially orthogonal to the pressure applicator 102. As described in greater detail below, once the locking tab 104 is in a substantially orthogonal plane to the pressure applicator 102, the aperture or opening 12 that is formed within the locking tab 104, and through which the pressure applicator 102 is disposed, becomes substantially orthogonal to the pressure applicator 102 and permits the pressure applicator 102 to freely slide through the locking tab's aperture or opening 126 and the mounting plate's aperture or opening 107 through with the pressure applicator 102 is disposed.

In another embodiment of the invention, the locking tab 104 may be attached to the mounting plate 106 via an integrally formed tab extension portion 120 and tab holder 122. In other embodiments, the tab extension portion 120 and tab holder 122 may not be integrally formed, but may be attached via an attachment mechanism. As illustrated in FIG. 4, for example, the tab extension portion 120 may extend from the top surface of the mounting plate 106 (i.e. the surface that is faced away from the wound when the apparatus 100 is placed over the wound). A tab holder 122, which may be integrally formed or attached to the tab extension portion 120 may be comprised of a slot to accept the locking tab 104 and mate with it. As illustrated in FIG. 4, the tab holder 122 may mate with the locking tab 104 in a manner that the locking tab 104 may be moved in a downward direction by depressing the locking tab 104 at an end that is not connected to the tab holder 122, thereby permitting the locking tab 104 to be placed in a plane that is substantially orthogonal to the pressure applicator 102. As described in greater detail below, once the locking tab 104 is in a substantially orthogonal plane to the pressure applicator 102, the aperture or opening that is formed within the locking tab 104, and through which the pressure applicator 102 is disposed, becomes substantially orthogonal to the pressure applicator 102 and permits the pressure applicator 102 to freely slide through the locking tab's aperture or opening and the mounting plate's aperture or opening through with the pressure applicator 102 is disposed.

The mounting plate 106 may also be comprised of articulating strap attachment point(s) 114, which serve to couple the mounting plate 106 to straps that may be attached around a patient. In one embodiment of the invention, the one or more articulating strap attachment point(s) 114 may extend downward from the bottom surface of the mounting plate 106 (i.e. the surface that faces the wound site when the apparatus 100 is placed over a patient's wound).

Figure 3:
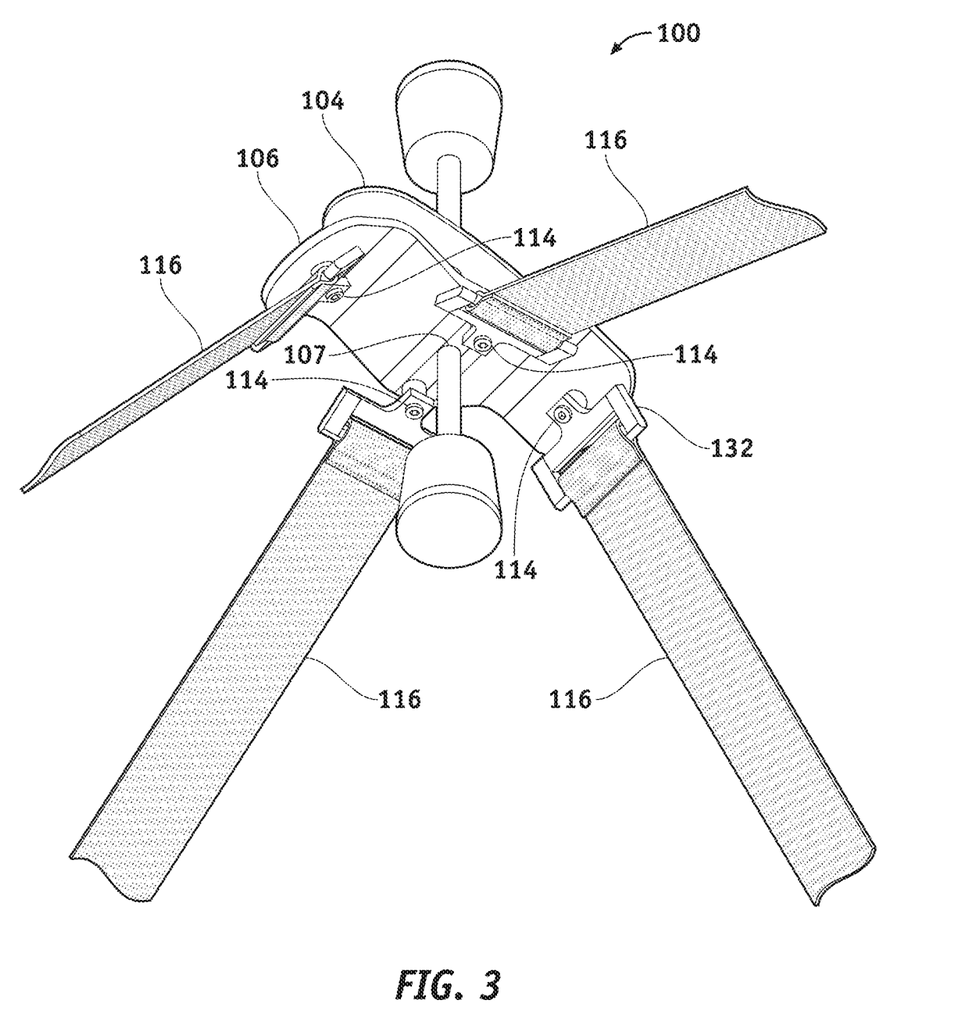
FIG. 3 illustrates an exemplary apparatus from another perspective, in accordance with an embodiment of the invention.

Now referring to the articulating strap attachment point(s) 114 as illustrated in FIGS. 1 and 3. As discussed herein, the articulating strap attachment point(s) 114 extend downward from the bottom surface of the mounting plate 106 (i.e. the surface that faces the wound site when the apparatus 100 is placed over a patient's wound). In accordance with an embodiment of the invention, the articulating attachment point(s) 114 form a coupling mechanism to permit a portion of one or more straps 116 to connect to the mounting plate 106. Specifically, as illustrated in FIG. 3, the articulating attachment point(s) 114 couple to buckles 132 that may be further connected to straps 116. In one embodiment of the invention, the strap buckles 132 are comprised of an aperture or an opening. The buckle's aperture may be placed over an articulating strap attachment point 114, and the attachment point 114 may thereafter be locked by a screw, a bolt mechanism, or another similar system to ensure that the straps 116 do not become inadvertently disconnected from the mounting plate 106. In one embodiment, the diameter of the buckle's 132 aperture may be slightly larger than the exterior diameter of the articulating strap attachment point(s) 114, wherein the aperture is substantially circular and the articulating strap attachment point(s) 114 are substantially cylindrical. This feature of the present invention permits the strap buckles 132 and the mounting plate 106 to rotate around each other along a central axis.

Figure 2A:
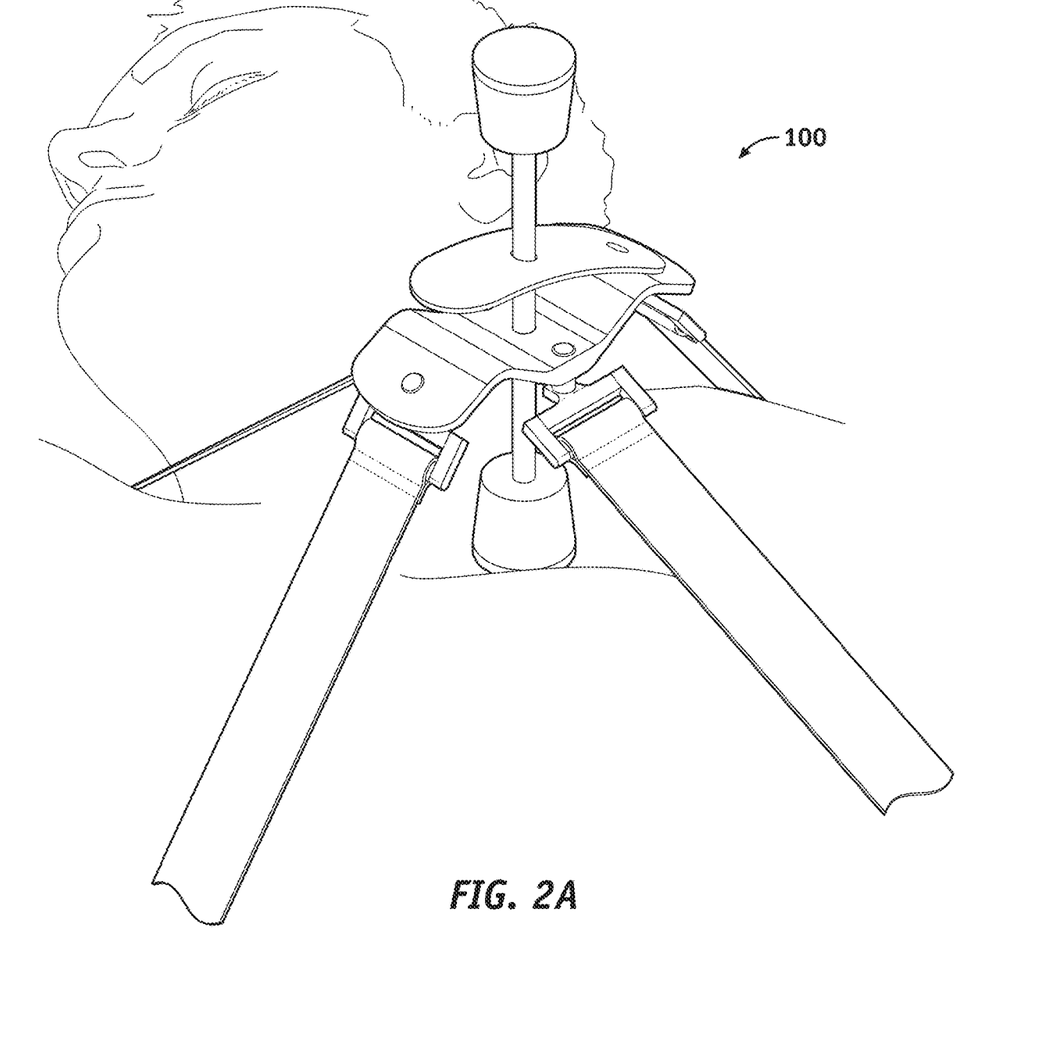
FIG. 2a illustrates, in accordance to one embodiment of the invention, an exemplary apparatus that is connected to a patient's shoulder to apply point-pressure on the patient's aorta.
Figure 2B:
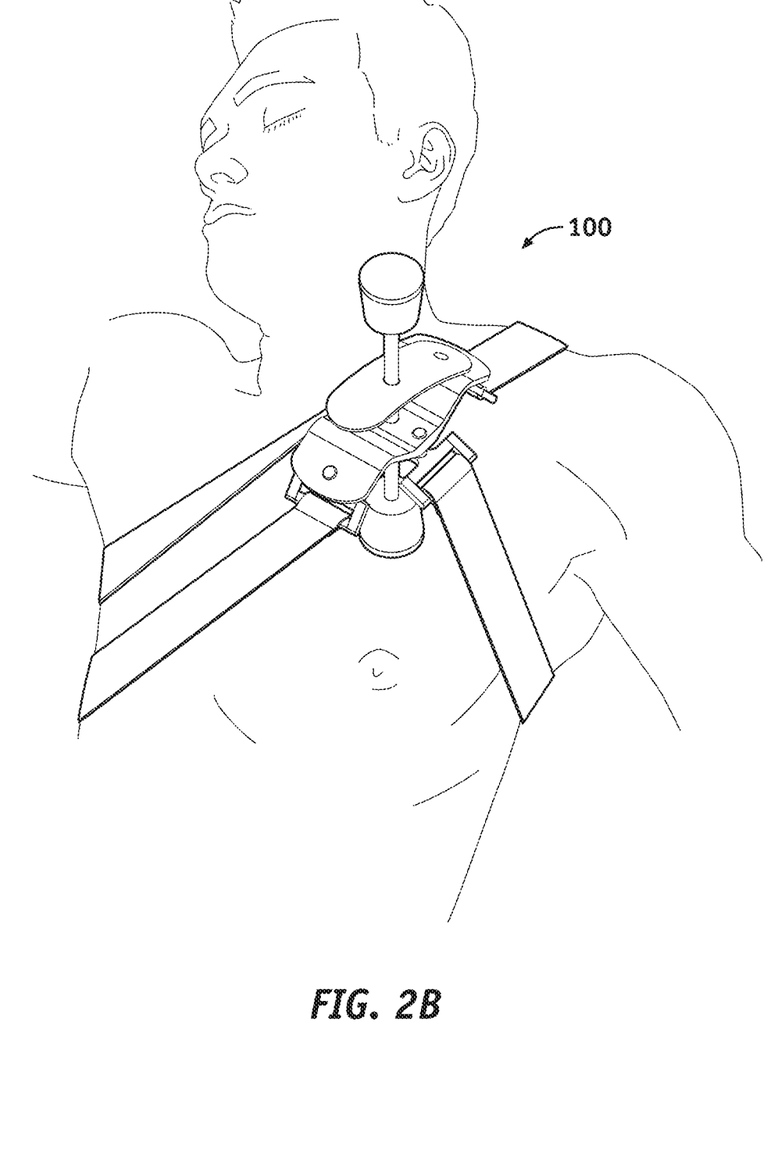
FIG. 2b illustrates, in accordance with an embodiment of the invention, an exemplary apparatus that is attached to a patient's torso to apply point-pressure on the patient's subclavian artery.
Figure 2C:
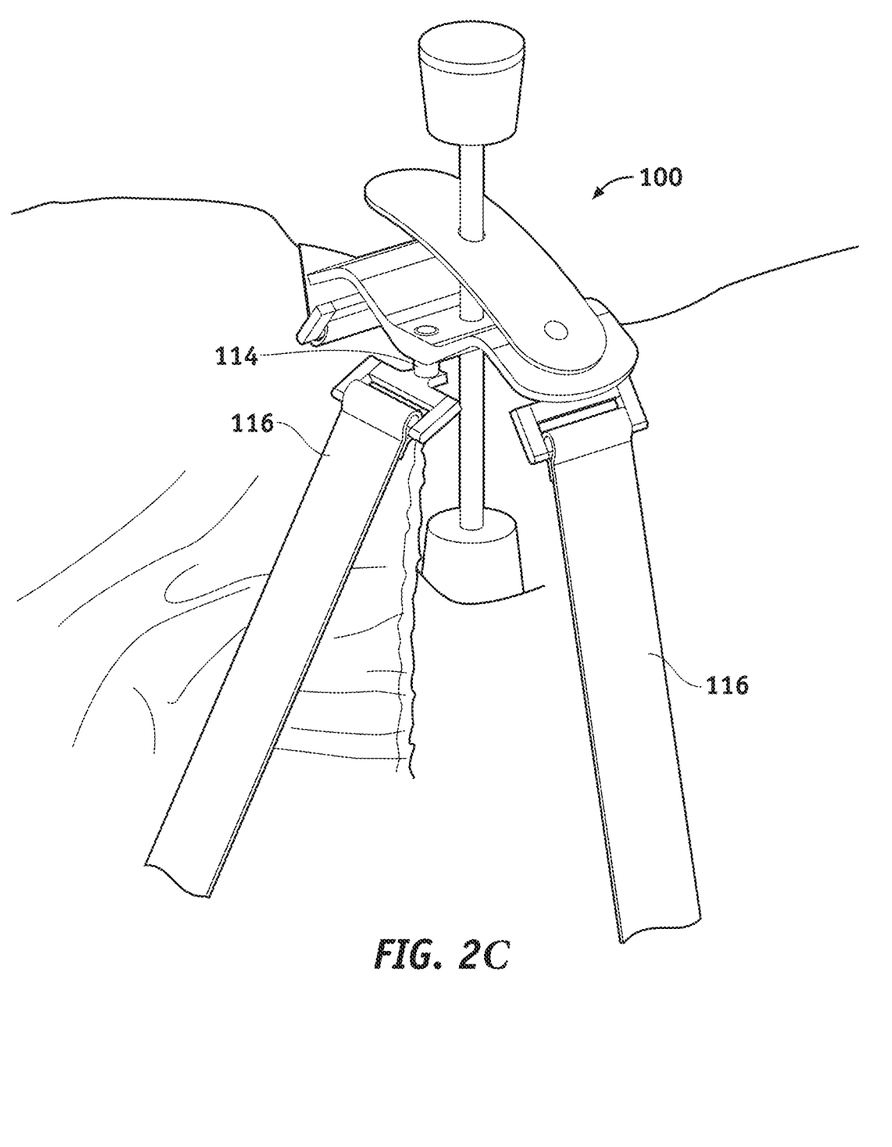
FIG. 2c illustrates, in accordance with an embodiment of the invention, an exemplary apparatus that is attached to a patient's torso to apply point-pressure on the patient's abdominal aorta.

The coupling mechanism of the present invention enables the apparatus to securely fit over a variety of different portions of a patient's body and/or body parts, and permits the apparatus 100 to remain substantially parallel to wound. FIGS. 2a, 2b, and 2c highlight this point by illustrating the apparatus 100 as being securely fastened to a patient's throat and upper body, as shown in FIG. 2a, over the patient's chest to occlude the patient's subclavian artery, as illustrated in FIG. 2b, and over the patient's stomach to occlude the abdominal aorta, as illustrated in FIG. 2c. These figures are exemplary to illustrate how the apparatus may fit over a variety of different body parts and wound sites. However, the figures and the description herein is not limited to placement over these particular body parts or arteries. The apparatus 100 may be used over a variety of different parts of a user's body, including, but not limited to arteries in the pelvis where the pelvic bifurcation exists, a rotation at the attaching points to a parallel configuration with both around the waist is necessary to apply pressure to the abdominal vessels, the straps can then be rotated to be slightly off axis to allow one strap around the chest and one over the shoulder to apply pressure in the axilla. The same would be necessary to apply pressure to the subclavian artery. The rotation permits the apparatus 100 to apply pressure in nontraditional locations such as heavy venous bleeding from lower abdominal mid axillary wounds or buttocks wounds or caring for large patients.

In one embodiment, the apparatus 100 may be comprised of four articulating strap attachment points 114. The four attachment points 114 may be disposed along the perimeter of the mounting plate's bottom surface. The four attachment points 114 redistribute the compressive force that may be applied by the straps 116 when they are securely fastened over a portion of the patient's body. In one embodiment, the four attachment points 114 enable the straps 116 to form an "X" pattern to cross under the apparatus 100 to stabilize the apparatus 100 when attached to a patient.

Figure 5:
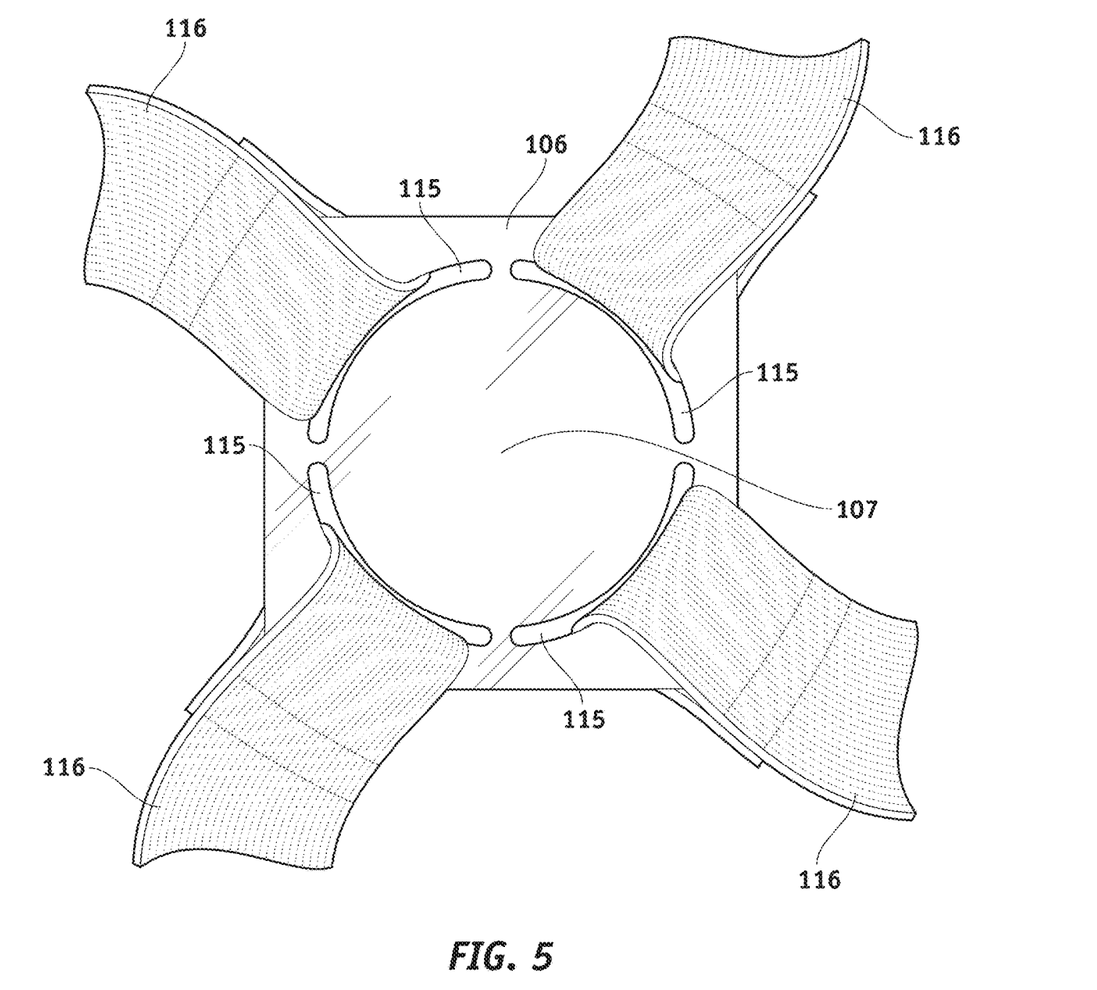
FIG. 5 illustrates an exemplary mounting plate of the inventive apparatus in accordance with an embodiment of the invention.

Now referring to FIG. 5, which illustrates another exemplary mounting plate with an attachment mechanism for attaching straps 116 to the apparatus 100. As illustrated, the mounting plate 106 may be comprised of one more slots 115. The straps 116 that secure the apparatus 100 around a patient's body can be fed through the slots 115 to connect the straps 116 to the mounting plate 106. The slots 115 may be extend around the outer parameter of the mounting plate 106 to permit the straps 116 to slide from one end of the slot 115 to another. This configuration permits a user to secure the apparatus 100 around a variety of different locations on a patient's body. For example, if one or more straps need to extend at a particular angle from the mounting plate 106 to be placed securely around the patient's body, then the straps may be sufficiently moved within the slot 115 to ensure that the apparatus 100 is properly secured against the patient's body.

This stability enhancing feature of the present invention (i.e. the features disclosed herein with regards to the mounting plate 106 and its connection to straps 116) also eliminates the need to carry a variety of different instruments to stop the bleeding at a variety of different portions of the patient's body. This is especially beneficial in emergency care settings where it is not economic (packing of bag space) or realistic to carry multiple devices in varying strap configurations to treat all the types of bleeding from different sites.

The stability enhancing features of the present invention also eliminate the need for a support plate, which is typically used with point-pressure systems. Traditional support plates were believed to be necessary and an integral part of point-pressure system. However, the inventor has identified a new system that eliminates the need for such components, and more importantly, reduces the number of items that a user or medical professional has the deploy and attach to user, especially when time is of the essence.

The stability enhancing features of the present invention enables the apparatus 100 to be used with a traditional tourniquet without require additional stability plates, etc. In one embodiment of the invention, the apparatus of the present invention 100 may be attached to a tourniquet. In these instances, the buckle closure system of traditional tourniquet may be replaced with the apparatus 100 for the application of point pressure.

In some embodiments of the invention, the mounting plate 106 is also comprised of at least one aperture or opening through which the pressure applicator may slide in an upward or a downward direction. The mounting plate aperture or opening is discussed in greater detail below in reference to FIGS. 1 and 4.

The mounting plate 106 may also be comprised of one or more finger hold(s) 108. In one embodiment of the invention, the finger holds 108 may be integrally formed on the bottom surface of the mounting plate 106 (i.e. the surface facing a wound when the apparatus 100 is disposed above the wound or an open blood vessel). The finger holds enable a user to apply counter-pressure (or upward force) to the apparatus 100. In one embodiment, the user may apply upward pressure on the finger hold(s) 108 and—at the same time—apply downward pressure on the pressure applicator 102 with the palm of his or her hand to slide the pressure applicator 102 in a downward direction. In one embodiment, applying downward force to pressure applicator 102 in a downward direction causes the locking tab 104 to disengage, which permits the pressure applicator 102 to travel in a downward direction (i.e. in the direction of the wound).

Referring now to the finger hold(s) 108 as illustrated in FIGS. 1 and 4 more particularly, which permit a user to apply counterforce when applying downward force on the pressure applicator. In one exemplary embodiment of the finger hold is molded into the mounting plate 106. The finger hold allows the user to apply counter force to the upper stop. The finger hold can also contain an aperture through which the rod is fed through, as well as be a affixing point for the lock tab.

The opposing force applied to the upper stop and finger hold 108 moves the rod through the lock tab and support base. Without this finger hold 108, downward force applied to the upper stop would move the device as a unit due to strapping being non-rigid and thus not force the rod through the lock tab and support base. Indeed, without the finger hold(s) 108 the apparatus 100 may not be able to apply sufficient force to extend the pressure applicator 102 to adequately stop the bleeding, while, at the same time, not cause damage to nearby tissue/wound, which could happen if the mounting plate 106 is pushed down on the wound site without application of counter-force.

The finger hold(s) 108 of the present invention also permit the apparatus 100 to meet several military spec requirements or desired attributes. For example, the strategically placed finger hold(s) 108, as illustrated in FIG. 1 permits a patient to apply pressure on his or her wound. In other words, it is possible to use the device single handedly as enabled by the finger holds(s) 108. This feature is beneficial in any strapping configuration and additionally allows the user to apply the devise to their-self in some instances, and allows for single hand tightening.

Any number of finger hold(s) 108 may be used without departing from the scope of the invention.

The locking tab 104 may connect to the mounting plate 106 or extension portions that are connected to the mounting plate, as illustrated in FIGS. 1 and 4, respectively. In one embodiment, the locking tab 104 is simply a plate with an aperture 126. The plate, in its normal or resting configuration rests at an angle that is offset from a plane that is orthogonal to the pressure applicator 102. The offset angle applies friction and pressure on the pressure applicator 102 and prevents the pressure applicator 102 from moving in an upward or downward direction relative to the mounting plate 106. When a user wishes to extend the pressure applicator 102 in either direction, the user may depress the locking tab 104 at the end that is not connected, directly or indirectly, to the mounting plate 106. Pressing the locking tab 104 in such a manner, aligns the aperture 126 to the pressure applicator 102 (i.e. places the aperture 126 in a plane that is substantially orthogonal to the pressure applicator 102. In one embodiment of the invention, the locking tab 104 automatically depresses whenever the pressure applicator 102 is also depressed by application of force by a user.

The locking mechanism described herein permits rapid application of pressure at a wound site. Unlike traditional prior art systems, which apply pressure slowly or gradually, the auto-locking mechanism of the present invention permits users to apply pressure extremely rapidly and by simply applying downward pressure on the pressure applicator. Moreover, unlike other pressure application systems, which are unreliable in transport scenarios and the like, the pressure application system of the present invention permits universal use in a variety of different combat, transport, and other scenarios.

The present disclosure is also for a method of using the apparatus 100 disclosed herein. The method is comprised of placing the apparatus 100 over a wound or an open blood vessel, attaching the apparatus 100 to the straps are may be disposed around a patient's body, applying downward pressure on the pressure applicator, applying counter pressure (or upward pressure) to the mounting plate 106 via provided finger holds Additional Considerations As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has." "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary. "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for creating an interactive message through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

What is claimed is:

1. An auto-locking apparatus for controlling hemorrhage, the apparatus enabling a user to apply point pressure extremely rapidly with a single hand, the apparatus comprising:

a mounting plate for mounting the apparatus over a wound site, the mounting plate comprising a top surface and a bottom surface;

an articulating strap attachment point extending from the mounting plate, the articulating strap attachment point connecting to a buckle on a strap that secures the apparatus over the wound site, the mounting plate and the buckle configured to freely rotate around each other when the mounting plate and the buckle are connected to the articulating strap attachment point, the articulating strap attachment point thus ensuring that the mounting plate remains parallel to the wound site when the apparatus is secured to a patient;

a pressure applicator for applying point pressure to the wound site, the pressure applicator extending through the mounting plate and being stabilized in a lateral direction by the mounting plate;

an auto-locking mechanism enabling the pressure applicator to travel, upon application of downward force, towards the wound site when the apparatus is placed over the wound site, the auto-locking mechanism preventing the pressure applicator from travelling away from the wound site when downward pressure is removed from the pressure applicator, the auto-locking mechanism comprising a locking tab; and a finger hold disposed on the mounting plate, the finger hold enabling a user to apply counter-force in a generally opposite direction to the downward force that may be applied to the pressure applicator, the counterforce enabling a user to apply leverage when applying downward force to the pressure applicator.

2. The apparatus of claim 1, wherein the mounting plate is further comprised of an aperture or opening that extends from the top surface of the mounting plate to the bottom surface of the mounting plate.

3. The apparatus of claim 2, wherein the pressure applicator travels through the aperture or opening in the mounting plate.

4. The apparatus of claim 1, wherein the pressure applicator is further comprised of a gripper that is disposed on the distal end of the pressure applicator, the gripper comprised of a compressible material.

5. The apparatus of claim 1, wherein the pressure applicator is further comprised of a hemorrhage stopper that is disposed on the proximal end of the pressure applicator, the hemorrhage stopper stopping hemorrhage at the wound site upon application of force.

6. The apparatus of claim 1 wherein the locking tab of the auto-locking mechanism is further comprised of an aperture or opening.

7. The apparatus of claim 6, wherein the pressure applicator travels through the aperture or opening in the locking tab.

8. The apparatus of claim 7, wherein the locking tab extends at an angle at a resting position, the angle enabling the locking tab to apply friction to the pressure applicator and prevent it from moving longitudinally through the locking tab's aperture or opening.

9. The apparatus of claim 8, wherein the friction applied on the pressure applicator by the locking tab may be removed by applying downward pressure on the locking tab, which places the locking tab on a plane that is orthogonal to the pressure applicator.

10. The apparatus of claim 6, wherein the locking tab extends from a tab holder, wherein the tab holder is connected to one end of the locking tab.

11. The apparatus of claim 10, wherein the tab holder extends from the mounting plate, the tab holder designed to hold the locking tab, by default, at an offset angle, which enables the locking tab to apply friction on the pressure applicator.

12. The apparatus of claim 11, wherein the tab holder is further comprised of vertical headroom, which permits the locking tab to be depressed at an end that is not connected to the tab holder, thereby placing the locking tab in a plane that is substantially orthogonal to the pressure applicator.

13. The apparatus of claim 1, wherein the finger hold is molded into the mounting plate.

14. The apparatus of claim 1, wherein the finger hold is comprised of an aperture or opening, wherein the pressure applicator travels through the aperture or opening in the mounting plate and the aperture or opening in the finger hold.

15. The apparatus of claim 1, wherein the apparatus is comprised of four articulating strap attachment points.

16. The apparatus of claim 15, wherein each articulating strap attachment point connects to a buckle, each buckle being connected to a strap.

17. The apparatus of claim 16, wherein the straps connect together around a patient to secure the apparatus over a wound site.

18. The apparatus of claim 17, wherein, when the straps are secured around the patient, the articulating strap attachment points permit rotation to ensure that the apparatus remains substantially parallel to the surface of the wound site.

* * * * *